(12) United States Patent
Powlan (10) Patent No.: US 8,308,733 B1
(45) Date of Patent: Nov. 13, 2012

(54) DEVICE AND METHOD FOR LOCKING INTRAMEDULLARY NAILS

(76) Inventor: Roy Y. Powlan, Lafayette, CA (US)

( * ) Notice: Subject to any disclaimer, the term of this patent is extended or adjusted under 35 U.S.C. 154(b) by 0 days.

(21) Appl. No.: 13/373,960

(22) Filed: Dec. 6, 2011

(51) Int. Cl.
*A61B 17/90* (2006.01)
(52) U.S. Cl. .................. 606/96; 606/97; 606/98; 606/87
(58) Field of Classification Search .................. 606/87, 606/96–98, 102
See application file for complete search history.

(56) References Cited

U.S. PATENT DOCUMENTS

| | | | |
|---|---|---|---|
| 5,031,203 | A | 7/1991 | Trecha |
| 5,212,720 | A | 5/1993 | Landi |
| 5,426,687 | A | 6/1995 | Goodall |
| 5,661,775 | A | 8/1997 | Cramer |
| 2011/0077657 | A1 | 3/2011 | Karasik |

*Primary Examiner* — Thomas Barrett
*Assistant Examiner* — Michael T Schaper (57) ABSTRACT

The device with an adjustable bi-rotatable base assembly, aligns the central longitudinal axis of a drilling device with the axis of an x-ray beam that is coaxial with the axis of a line that extends through the distal openings of an intramedullary nail that has been inserted into the cavity of a tubular bone.

6 Claims, 5 Drawing Sheets

DEVICE AND METHOD FOR LOCKING INTRAMEDULLARY NAILS

FIELD OF THE INVENTION

This invention relates to locating the openings in the distal end of an implanted intramedullary nail, and to the means for inserting transfixing screws through the openings.

BACKGROUND AND RELATED TECHNOLOGY

The treatment of choice for fractures of the shaft of the femur is the intramedullary (IM) nail, a long tubular rod that spans the fracture and often needs to be fastened to the bone at both ends with transverse screws placed through openings at both the proximal and distal ends of the nail. The screws at the proximal end are close to the surgical incision and are fairly easy to insert, but the openings at the distal end, hidden as they are, deep within the bone and soft tissues, present a challenge to locate and to place screws through them. As a result, there have been numerous inventions attempting to solve this problem, the commonest being an external side arm drill jig, in which a long arm placed external to the patient's limb and parallel to the nail, is fastened to the proximal end of the nail, while the distal end of the arm comprises a drill jig, which is expected to line up with the nail openings. Unfortunately, the nail often bends and twists during its insertion and as a result, the openings are not where they were expected to be, rendering the jig useless. Other similar inventions have used adjustable side arms to compensate for this bending and twisting, with or without the use of x-rays to help align the arms and their drill jigs with the nail openings. Typical of these is US 2008/0281331 A1.

Other inventions used small magnets placed within the distal end of the nail, and which are sensed with other magnets to help locate the openings in the IM nail such as U.S. Pat. No. 7,753,913.

Still other inventions used electromagnetic coils placed within the distal end of the nail, which are sensed and their signal displayed on a monitor to show the location of the openings and direct a drill guide such as U.S. Pat. No. 7,060,075.

Others use x-rays to locate the openings in conjunction with co-axial laser beams to assist in the placement of a drill to bore openings in the bone in line with the openings in the nail, such as U.S. Pat. No. 5,426,687. Many of these systems use a remote monitor to display the rod openings, and require the surgeon to manipulate a drill freehand while watching the display, relying on the surgeon's skill to find the openings in the IM rod, such as U.S. Pat. No. 4,803,976.

Others use a C-arm fluoroscope and computers to calculate the location of the openings in the IM nail and then instruct a robot to drill the openings in the bone based on this information, an approach too expensive for many hospitals. Examples are US 2008/0281334 A1, and US 2009/0043190A1.

Currently, many surgeons prefer to use the tried and true method of using the C-Arm fluoroscope to locate the openings and then use a drill freehandedly to drill the openings in the bone and insert the screws. In this method, a C-arm fluoroscope is rotated around the limb, providing instant images which can be viewed on a monitor. In use, the C-arm shows the distal end of the nail and its screw openings. The C-arm is then manipulated until the openings on both sides of the nail become superimposed on each other, creating an undistorted "perfect circle", which proves that the x-ray beam is properly aligned with the openings. In a slight variation of this technique, thought to be a little faster, radio-opaque wires are taped to the image intensifier receiver, perpendicular to each other and centered on the receiver. The C-arm is then manipulated until the nail openings are centered on each other and over the crossed wires, which is proof that the central x-ray beam is aligned with the openings. A pencil mark or an incision, or both, is made on the skin over the displayed opening and through it, a drill is hopefully aligned freehand with the x-ray beam and an opening made through the bone, and, depending on skill and luck, through the opening in the nail and the opposite bone cortex. Often, however, multiple attempts are required, and it has been estimated that this phase of the operation takes more time than the rest of the operation, with more x-ray exposure to the surgeon, the staff and the patient, as well as the added expense.

The present invention is a targeting device in which the targeted location is not the actual location of the openings in the distal end of the IM nail as in the prior art, but is instead, the location of the x-ray beam on the outer surface of the thigh as it traverses the surface and through the "perfect circles" that the nail openings create when exhibited on the fluoroscope's monitor.

SUMMARY OF THE INVENTION

A C-arm fluoroscope is first used as usual, to display the "perfect circles" and their position relative to the lateral surface of the thigh as displayed on the monitor, is marked on the lateral thigh with a sterile marker This invention is based on the recognized fact that every drill, Steinmann pin, or other elongate tool that is being used to translate through the openings in the nail must necessarily pass through this exact location on the outer thigh if it is to become aligned with the opening in the IM nail. The further information that is needed is the location of the X and Y coordinates on the base of an imaginary cone whose apex is at this location on the outer thigh, and it is the function of the present invention to not only provide this information, but also to employ a drilling device to act on this information, eliminating the need for a hand-held drill and its inherent inaccuracies.

The present invention comprises a targeting device that is mounted on a known sturdy floor stand having a sturdy elevating, rotating, and tilting head, similar to those commonly used with instrument or camera tripods.

The targeting device comprises a target which comprises a small radio-opaque spherule, in one embodiment, 5 mm. in diameter, mounted a short distance, in one embodiment, 5 cm., in front of the targeting grid so that the relationship of the location of the spherule to the grid can be displayed on the C-arm monitor when x-rays pass through them. The distance between the spherical target and the grid can be varied, depending on the degree of accuracy required, e.g. the greater the distance, the greater the accuracy.

The target spherule and targeting grid are mounted on a bi-rotatable base, one part of which can be rotated through an arc, with the vertical axis of rotation coaxial with the target spherule, thus enabling the grid to move along the X-axis while the target spherule remains stationary in space.

A second part of the base is rotatable in the Y plane. The rotation is along an arc of a circle whose center is the target spherule, thus enabling the grid to move along the Y axis, while again, the target spherule remains stationary in space.

To use the device, the floor stand with the mounted device is positioned between the thigh and the C-arm x-ray emitter. Using the adjustable head of the device support, the target spherule and center of the targeting grid are positioned roughly coaxial with the estimated axis of the x-ray beam through the IM nail opening, and with the target spherule located immediately adjacent to, and touching the mark on the outer thigh previously made with the aid of the C-arm fluoroscope. The purpose of this rough preliminary alignment is to minimize the need for further adjustments of the aiming device.

It is important to note that because the target spherule is located on the vertical axis of the part of the base that rotates in the horizontal plane, and is also at the center of rotation of the part of the base that rotates in the vertical plane, the target spherule will always remains stationary relative to its location at the lateral thigh, even though the base is being adjusted in two planes.

A fluoroscopic image is then repeated displaying the position of the target spherule, relative to the targeting grid. The base is then adjusted, if necessary, by rotating the base in two planes so that the center of the grid is located exactly over the target spherule, as displayed on the monitor. This is easily accomplished because the base comprises index markings for both planes that correlate with both the horizontal and vertical grid lines, for example, one space of the index equals one space of the targeting grid.

When the target spherule is exactly centered on the grid, the device base is known to be parallel in two planes with the axis through the IM nail openings. The bi-rotatable base is then locked in this position, and the target and grid are removed from the base, having served their purpose.

A drill support with a slidingly attached drill is then releasably fastened to the adjusted device base. The drill slides on a linear track and its central drilling axis is dimensioned to be exactly coaxial with the axis between the target sphere and the center of the grid when they were previously in place, which in turn is coaxial with the x-ray beam through the openings in the intramedullary nail. As a result, any tools placed within the drill chuck such as a drill bit, Steinmann pins, drill sleeves etc. are automatically centered on the location on the outer thigh that is aligned with the axis of the x-ray beam through the IM rod opening. This eliminates the need for the surgeon to handle an unwieldy hand drill, as in the prior art, or exercise judgment as to its placement and angulation while watching a monitor. This is important because drilling through the skin and soft tissue such as muscle to reach the bone is unlike drilling through a solid substance where the trajectory, once established, does not change, whereas the weight and bulk of the drill when drilling in soft tissue may cause the drill tip to sag or wander slightly, so that even a few millimeters off course would result in its missing the nail hole completely.

The drill which is mounted on a track, is simply slid forward and back on its track to create the openings in the bone and through the openings in the IM nail. The drill is then used with accessories such as screw holders which are also aligned with the nail openings to insert the screws.

After the base of the targeting device and attached drill have been locked into coaxial alignment with the x-ray beam that had been used to facilitate the drilling of the bone and the insertion of the screws, the locked targeting device can then be used to calibrate that specific fluoroscopy machine for use in future similar surgeries with the minimal use of X-rays. The calibration can also be done using a simulated surgical set-up.

To accomplish this calibration, the direction of the drilling device on its track is reversed, so that the drill is facing the x-ray emitter. The drill bit or an equivalent long rod is placed in the chuck and the drill is advanced toward the face of the x-ray emitter until the end of the drill bit or rod touches a location on the face of the emitter indicating the exact source of the central x-ray beam. This location is then marked for future use of this particular fluoroscope in similar surgeries, because the exact x-ray source can vary with different machines.

In surgeries using the targeting device and a "marked" fluoroscope, the target of the targeting device is placed at the location of the "perfect circles" on the lateral thigh in the usual way, as displayed by the fluoroscope's monitor, The target and targeting grid are then replaced by the drill support and drill, with the long drill bit or rod in the drill chuck facing the x-ray emitter.

The base of the targeting device is then adjusted so that the end of the drill bit becomes aligned with the mark on the face of the emitter, and the base is then locked in this adjusted position. The axis of the drill is now coaxial with the former x-ray beam. The drill is redirected towards the thigh and the openings in the bone drilled in the usual manner.

In another embodiment of the targeting device where a "marked" or "calibrated" fluoroscopy machine is being used, the target and drill with the long drill bit that is used to align the targeting device with the axis of the x-ray beam through the openings of the intramedullary nail, are replaced with a similar target attached to a laser source, with the laser beam in effect replacing the function of the long drill bit. In use, the target is placed at the location on the thigh that corresponds to the "perfect circles". The targeting device base is then adjusted until the laser beam becomes aligned with the mark on the x-ray emitter, and the base is locked in place. The laser is then replaced with the drilling device and the openings in the bone are drilled in the usual manner.

While the present embodiment is manually adjustable, further embodiments could include a base that is adjustable with gears and thumb-wheels, or adjustable by means of servomotors, either directly or remotely controlled.

ADVANTAGES

The chief advantage of this invention is its mechanical simplicity. It is very easy to set up and supplement the currently used technique that employs a C-arm fluoroscope to align and display the distal intramedullary nail holes and as a result, is easy to learn and use.

It does not use complicated adjustable side-arm drill jigs, magnets or complicated electromagnetic sources inside and outside the nail, or dedicated computers and computer programs to locate the openings in the distal end of the intramedullary nail. It minimizes the exposure to the patient and surgical staff of x-rays when attempting to drill freehand, or attempting to follow the alignment of the drill on a monitor.

Since the drill alignment is automatically set and maintained on its track, it is more accurate.

It can be used with any brand of intramedullary nail unlike many proprietary devices that can be used with only one brand of nail.

It can be used for intramedullary nailing in any elongated tubular bone such as the femur or tibia.

Unlike the prior art using laser targeting to provide an axis for a hand drill, and require elaborate aiming devices to be affixed to the c-arm emitter, this invention simply uses the laser beam to align the adjustable base for use by a drill which is then automatically aligned.

DETAILED DESCRIPTION OF THE DRAWINGS

Figure 1:
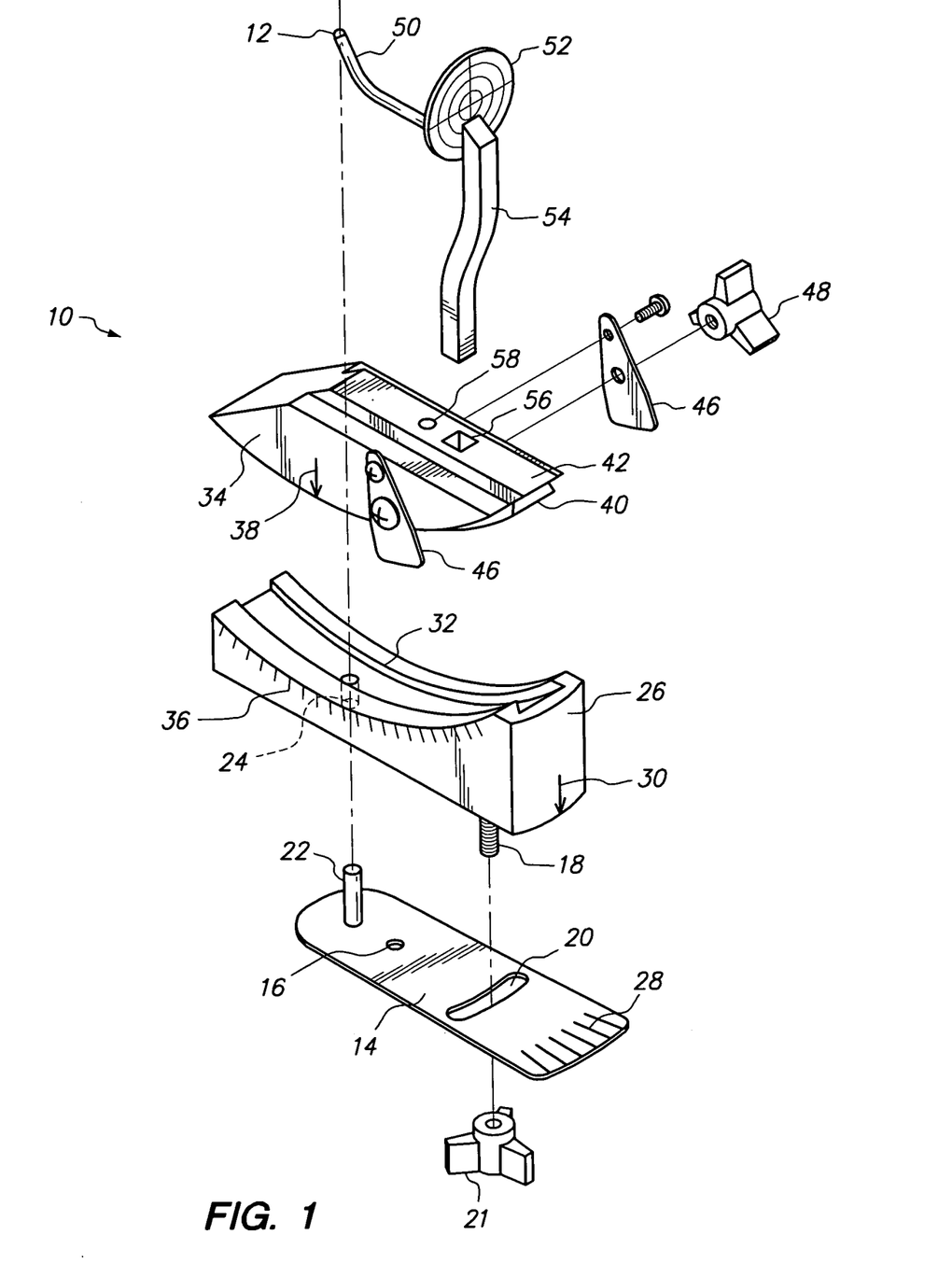
FIG. 1. A perspective exploded view of one embodiment of the complete device.

FIG. 1, an exploded view of the device, 10 illustrates the way in which a compact targeting device is adjustable in both the vertical and horizontal plane, and is able do this while a radio-opaque target 12, remains fixed in its position in space. The device comprises a base plate 14, which provides a support for the device. It comprises a threaded opening 16 for its releasable attachment to a known sturdy floor mounted support base, with a known sturdy adjustable head of the type commonly used with instrument or camera tripods. The base plate 10 also comprises a slot 20 to accommodate the threaded stud 18, which is clamped to the base plate 10 by the clamping knob 21. The base plate 10 also comprises an axle 22 which is slidingly fitted into the opening 24, and enables part 26, the second base component, to rotate through an arc of motion. Index markings 28 and indicator 30 display the amount of rotation in the horizontal plane of the second base component 26 around the vertical axis of axle 22.

The second base component 26 comprises a curved bearing surface 32 which is an arc of a circle whose center is located at target 12. This enables the congruent curved bottom surface 32 of the third component 34 of the base 10 to rotate around the target 12 in the vertical plane. The second component 26 also comprises index markings 36 which together with the indicator 38 displays the amount of rotation in the vertical plane.

The third component 34 of the base 10 cooperates with the second component 26 to rotate as described. The bearing surface 40 and bearing surface 32 are dove-tailed to enable sliding without other displacement. The top surface 42 is also dove-tailed to enable the locking engagement of drilling device holder 44 (shown on FIG. 5.)

Component 34 also comprises a locking clamp 46 and clamping knob 48 to lock the second and third components together following their adjustment.

A target 12 on an elongated arm 50 and a targeting grid 52 are releasably attached to the component 34 by means of a radio-transparent support 54, fitted into socket 56. The grid 52 comprises radio-opaque lines. It should be noted that the target 12 remains stationary in space when the base 10 is rotated in the vertical and horizontal planes, because it is located at the center of rotation of both rotating components of the base. Opening 58 is part of a fastener for the drill support 44.

All or part of the base can be comprised of, but not limited to, metal, plastic, or reinforced polymer, and capable of being sterilized.

Figure 2:
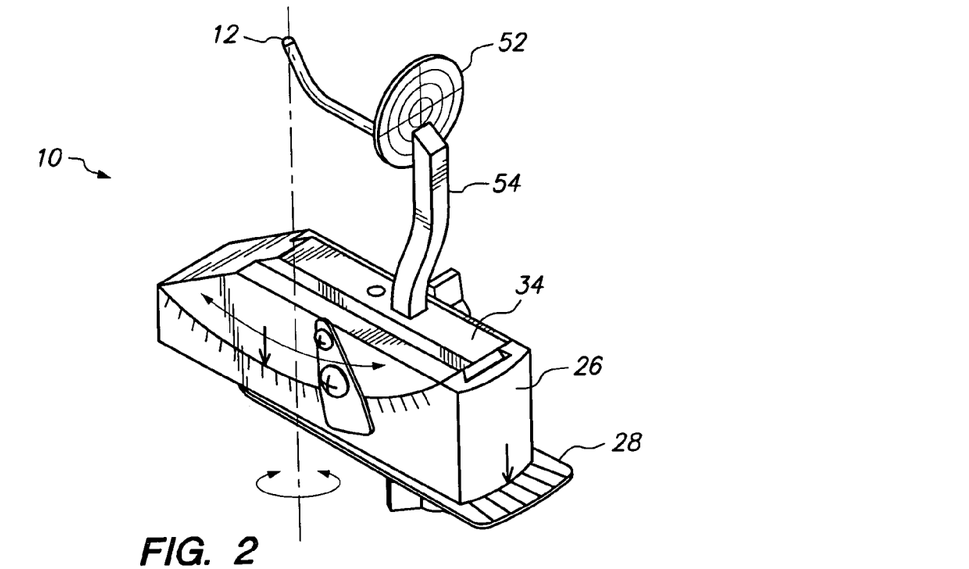
FIG. 2. A perspective view of one embodiment of the assembled device.

FIG. 2 shows the targeting device 10 fully assembled. Not shown is a known heavy floor stand with a known sturdy adjustable head. The arrows indicate potential motion in two planes.

Figure 3:
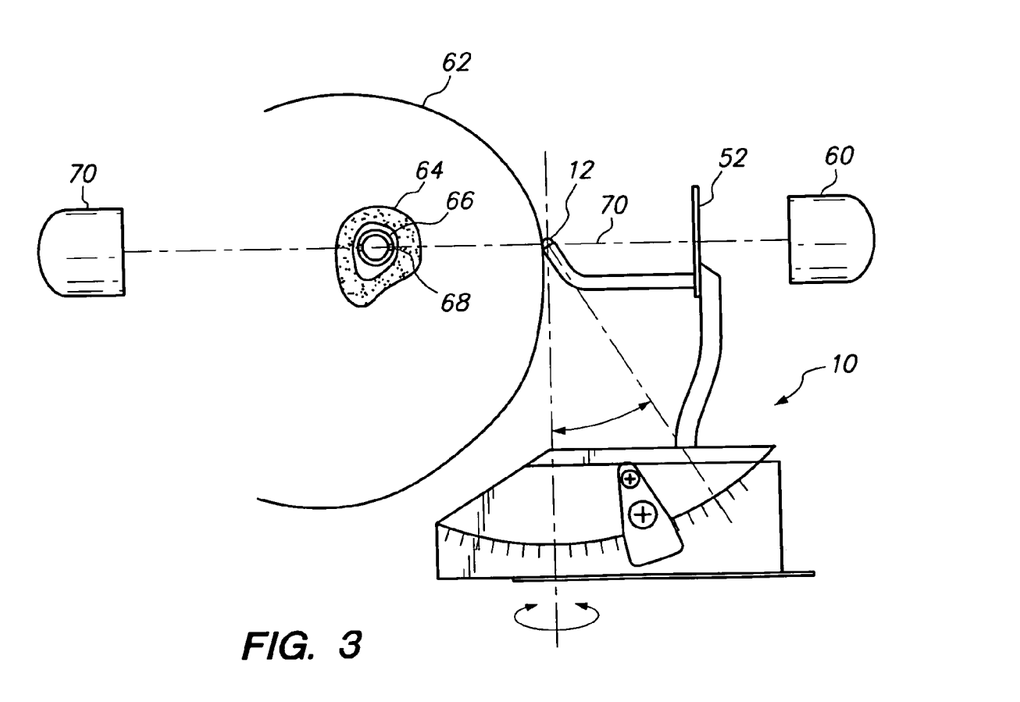
FIG. 3. Illustrates the typical placement of the device in use.

FIG. 3 shows the targeting device 10 in a typical position between the fluoroscopic emitter 60 and a cross-sectional view of the thigh 62, showing a cross-section of a tubular bone 64 containing an intramedullary nail 66 with an opening 68 on either side of the nail.

FIG. 3 also illustrates the x-ray beam 70 leaving the fluoroscopic emitter 60, traversing the center of the targeting grid 52, the target 12, the thigh 62, the bone 64, the openings 68 of the nail 66, and arriving at the fluoroscopic receiver 70, to be displayed on a monitor, (not shown).

Figure 4:
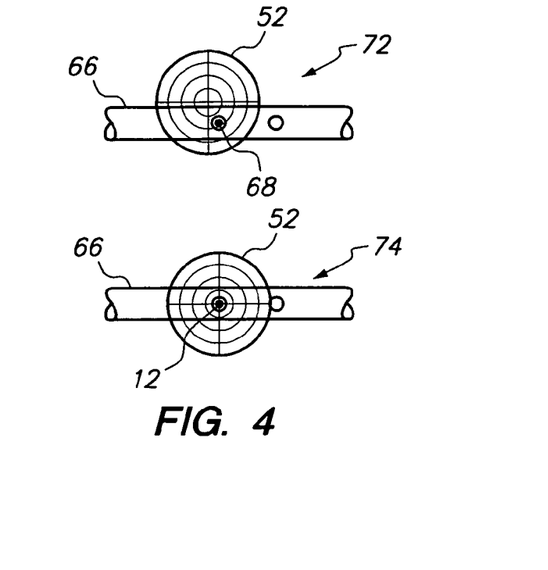
FIG. 4 Illustrates the display on the c-arm monitor before and after the device has been adjusted to place the target and the center of the targeting grid over the opening in the intramedullary nail.

FIG. 4 illustrates the view 72 on the fluoroscopic monitor before adjustment of the targeting device and the view 74 after adjustment where the targeting grid 52 is centered over the target 12, which in turn is centered over the opening 68 in the intra-medullary nail 66.

Figure 5:
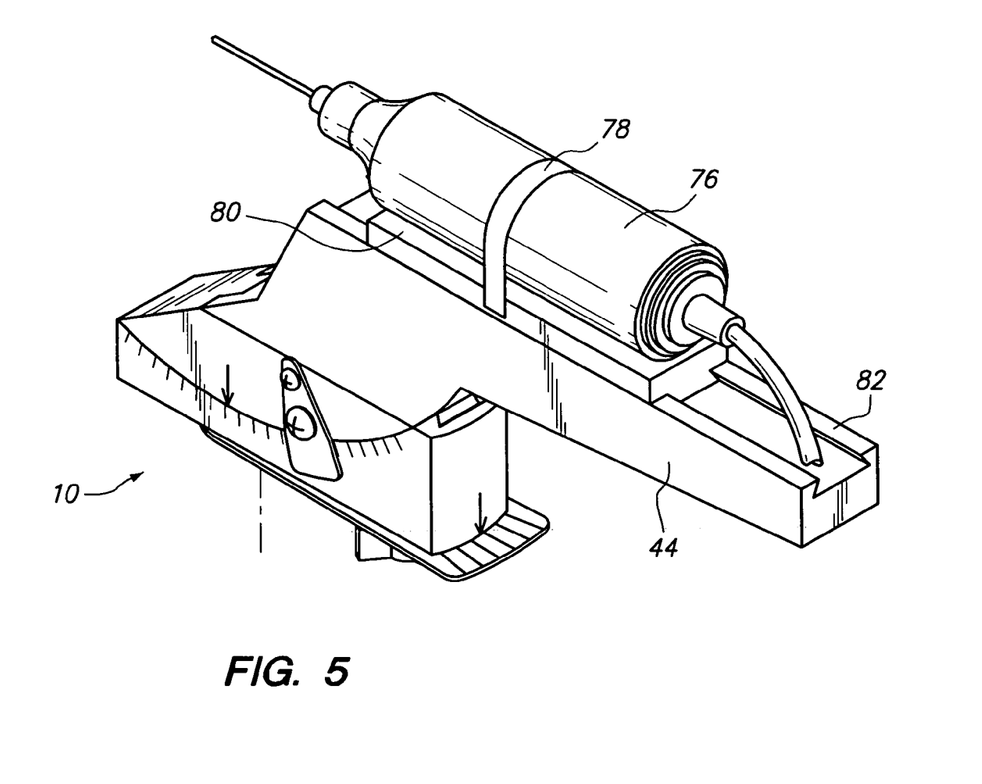
FIG. 5. A perspective view of the device in which the target and targeting grid have been replaced with a drilling device support and a drilling device.

FIG. 5 is a perspective view illustrating the targeting device 10 in which the target 12 and targeting grid 52 have been removed and have been replaced with the drilling device support 44 and the drilling device 76. The drilling device comprises a clamp 78 and a sled 80 that slides on a track 82. The drilling device support 44 and sled 80 are dimensioned to hold the drill 76 at a predetermined elevation and direction, with the longitudinal axis of the center of the drilling device coaxial with the axis of the x-ray beam known to be aligned with the openings in the intramedullary nail. The sled and track are dove-tailed to enable accurate longitudinal motion.

Figure 6:
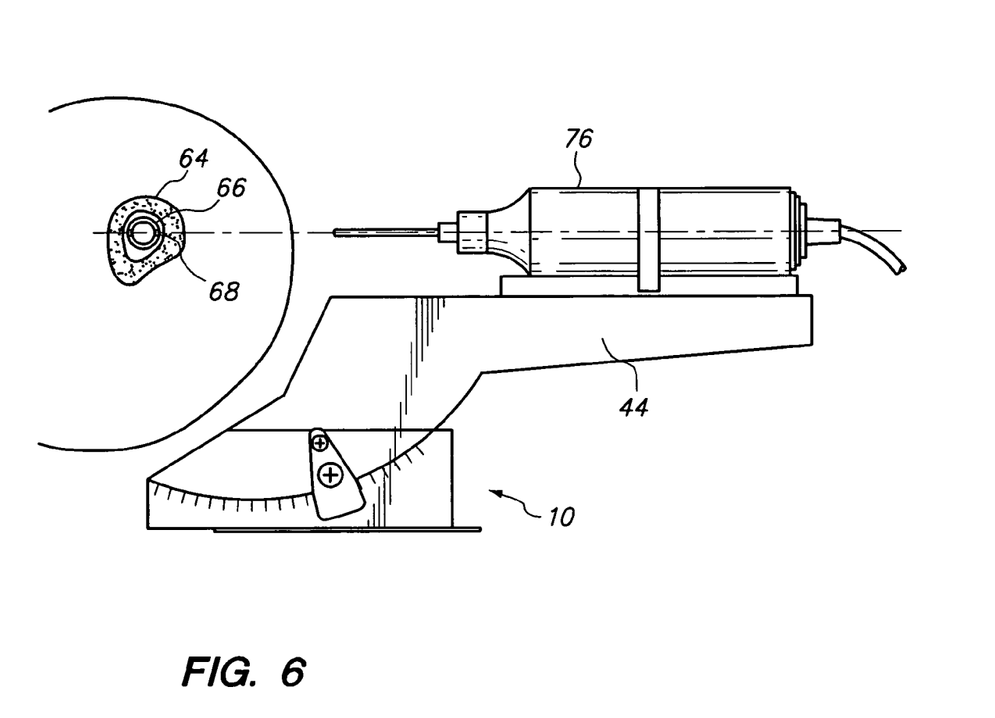
FIG. 6. A view illustrating the typical placement of the device and drill after adjustment and alignment of the base.

FIG. 6 illustrates the targeting device 10 together with the drilling device support 44 and the drilling device 76 having been releasably attached to the base. The base has been adjusted and aligned with the openings 68 of the intramedullary nail 66. The drilling device is prepared to drill through the soft tissue and bone 64 and the openings 68 in the intramedullary nail 66.

Figure 7:
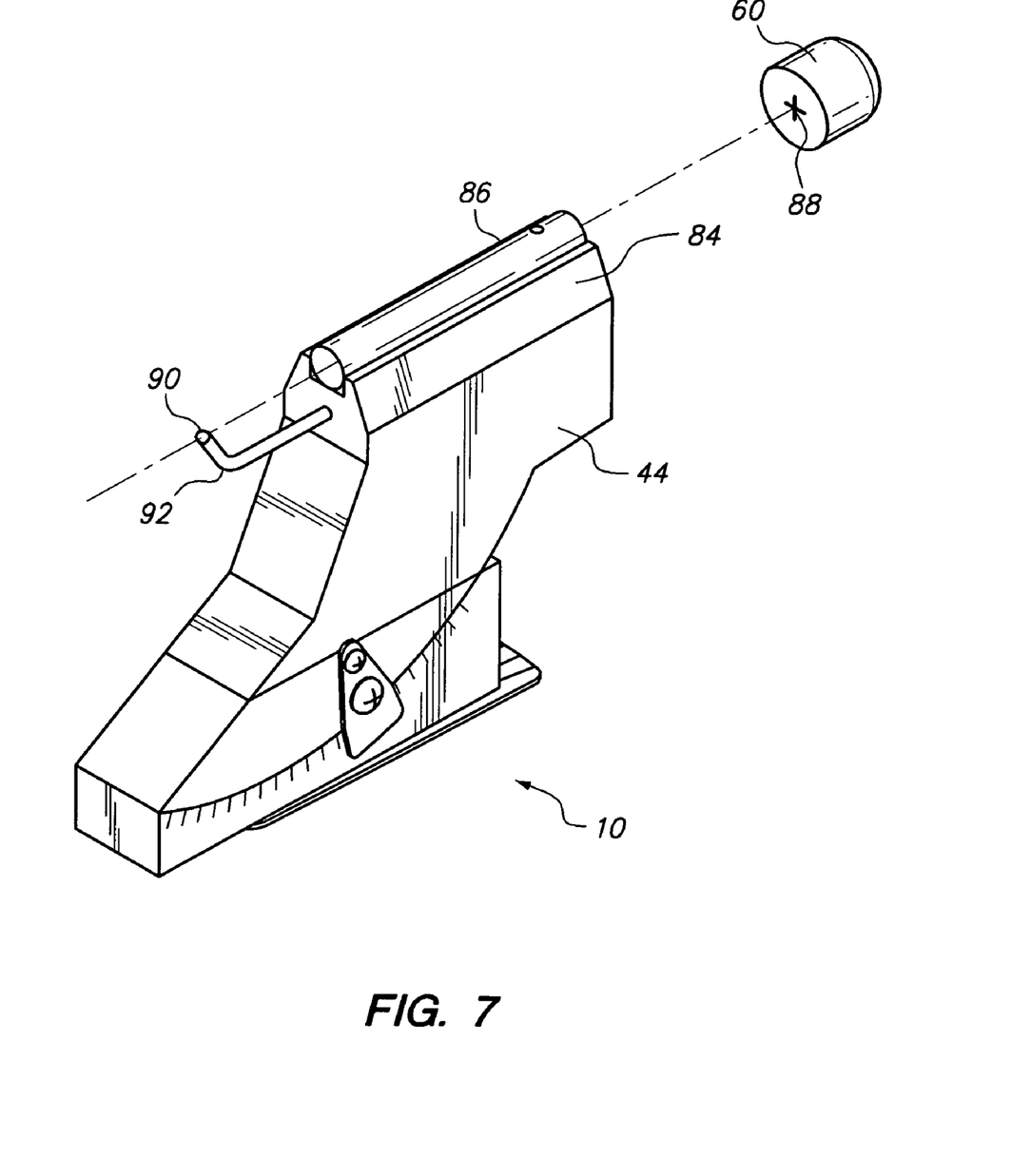
FIG. 7. A perspective view of another embodiment of the device using a laser beam aimed backwards toward the source of the central x-ray of the emitter.

FIG. 7 illustrates a laser support 84 with a laser source 86 that have replaced the targeting grid 52 and is positioned to project a laser beam towards a mark 88 on the surface of the x-ray emitter 60 that signifies the source of the central x-ray beam. This enables the base of the targeting device 10 to be adjusted so as to be parallel with the central x-ray beam. The target 90 is supported by an arm 92 that is attached to the laser support 84 at the end away from the laser source 86, and is positioned at the junction of the vertical and horizontal axes of the adjustable base.

This laser accessory 84 and 86 of the targeting device 10 is used in conjunction with a c-arm fluoroscope that has had the exact source of the central x-ray beam 88 from the emitter 60 marked on the face of the emitter.

| | Part Names. |
|---|---|
| 10 | Targeting device |
| 12 | Radio-opaque target |
| 14 | Base plate |
| 16 | Threaded opening in base plate |
| 18 | Threaded stud |
| 20 | Slot |
| 21 | Clamping knob |
| 22 | Axle |
| 24 | Opening for axle |
| 26 | Second component of base |
| 28 | Index markings |
| 30 | Indicator |
| 32 | Curved bearing surface |
| 34 | Third component of base |
| 36 | Index markings |
| 38 | Indicator |
| 40 | Bearing surface |
| 42 | Top surface of 3rd component |

-continued

| Part Names. | |
|---|---|
| 44 | Drilling device support |
| 46 | Locking clamp |
| 48 | Clamping knob |
| 50 | Target support arm |
| 52 | Targeting grid |
| 54 | Target grid support |
| 56 | Socket |
| 58 | Fastener for drill support |
| 60 | Fluoroscopic emitter |
| 62 | Cross section of limb |
| 64 | Cross section tubular bone |
| 66 | Intramedullary Nail |
| 68 | I.M. Nail openings |
| 70 | Fluoroscopic Receiver |
| 72 | View before adjustment |
| 74 | View after adjustment |
| 76 | Drilling device |
| 78 | Drilling device clamp |
| 80 | Sled |
| 82 | Track |
| 84 | Laser support |
| 86 | Laser source |
| 88 | Mark on Emitter face |
| 90 | Target on laser support |
| 92 | Target support arm. |

What I claim is:

1. An orthopedic apparatus for positioning a longitudinal central axis of a bone drilling device into coaxial alignment with an axis of an x-ray beam that is coaxial with a line through distal openings of an intramedullary nail that has been inserted into a cavity of a tubular long bone, comprising:

an adjustable bi-rotatable base assembly, said base assembly comprising a first component, said first component comprising a base plate, said base plate comprising a first end and a second end, and with a superior surface and an inferior surface, and with the second end comprising a vertically disposed cylindrical axle defining a vertical axis, said axle comprising a first end and a second end, and with the first end of the axle fixedly attached to the superior surface of the base plate, the base assembly also comprising an elongate second component, said second component comprising an elongate element with a first end and a second end, and with a superior surface and an inferior surface, and with the inferior surface of the second end of the elongate element comprising an orifice for cooperating rotatably with the axle of the base plate, and with the inferior surface of the second component contiguous in a rotatable sliding relationship with the superior surface of the base plate, and with the superior surface of the second component comprising arc-like surfaces having a longitudinal arc-like configuration;

the base assembly also comprising a third elongate component comprising a first end and a second end, and a superior surface and an inferior surface, and with the inferior surface of the third elongate component comprising arc-like surfaces having a longitudinal arc-like configuration that is congruent with, and in apposition with, the superior surface of the second component and with a horizontal line through the center of rotation of the arc-like surfaces of the elongate second component and third elongate component comprising a horizontal axis and with said horizontal axis intersecting with the vertical axis of the axle of the base plate, wherein the superior surface of the third component comprises a targeting assembly, said targeting assembly comprising a support rod, said support rod comprising a first end and a second end, and with a target and a targeting grid mounted on the second end of said support rod, and with the first end releasably fastened to a longitudinal midline of the superior surface of the third elongate component, and with said target comprising a bead-like radio-opaque spherule also positioned on the longitudinal midline, and positioned at the intersection of the vertical axis of the axle of the base plate and the horizontal axis of the center of rotation of the arc-like surfaces of the second and third components, wherein the targeting grid is positioned on, and perpendicular to, the longitudinal midline, and positioned a pre-determined distance away from the target, said targeting grid comprising a series of radio-opaque grid lines on a radio-transparent substrate, and with the center of the targeting grid positioned on a line extending through the bead-like radio-opaque spherule and parallel to the longitudinal midline of the superior surface of the third elongate component, wherein the bead-like radio-opaque spherule is positionable in apposition to a surface marking on a surface of a leg, said marking indicative of the axis of the x-ray beam passing through said marking and said distal openings of the intramedullary nail that has been inserted into the cavity of the tubular long bone, the base assembly also comprising an elongate fourth component comprising an elongate drilling device support, said support comprising a superior surface and an inferior surface, and with means for the releasable attachment of its inferior surface to the superior surface of the third component, said means comprising a threaded fastener, and with the superior surface of the elongate fourth component comprising a sled and being configured to support a sled mounted motorized drill, said sled comprising an elongate member with a superior surface and an inferior surface, and with the inferior surface of the elongate member configured to enable a sliding cooperation with the superior surface of the third component along their longitudinal axes, and with the superior surface of the elongate member comprising a circular clamp, said clamp configured to maintain said motorized drill in a longitudinal position, with the central longitudinal axis of the drill coaxial with said line through said bead-like radio-opaque spherule and center of the targeting grid.

2. An orthopedic apparatus of claim 1 wherein the first end of said base plate comprises first index markings and the first end of said second component comprises a first indicator, said first index markings and first indicator indicating the amount of rotation of the second component on the base plate, wherein the second component comprises second index markings along an edge of the arc-like surfaces of the second component and wherein the third component comprises a second indicator on an edge of the arc-like surfaces of the third component, said second index markings and second indicator indicating the amount of rotation of the third component on the second component, and with the first and second index markings indicating the amount of the horizontal and vertical rotation of the base assembly around the bead-like radio-opaque spherule, and with the spacing of said first and second index markings correlated with the spacing of the radio-opaque grid lines of the targeting grid.

3. An orthopedic apparatus of claim 1 wherein the base plate comprises a threaded means, said means comprising a threaded orifice for the releasable attachment of an adjustable floor stand with an elevating, rotating and tilting head.

4. An orthopedic apparatus of claim 1 in which the apparatus is comprised of metal, plastic, or reinforced polymer and capable of being sterilized.

5. An orthopedic apparatus for positioning a longitudinal central axis of a drilling device into coaxial alignment with an axis of an x-ray beam that is coaxial with a line through distal openings of an intramedullary nail that has been inserted into a cavity of a tubular long bone, comprising an adjustable bi-rotatable base assembly, said base assembly comprising a first component, said first component comprising a base plate, said base plate comprising a first end and a second end, and with a superior surface and an inferior surface, and with the second end comprising a vertically disposed cylindrical axle defining a vertical axis, said axle comprising a first end and a second end, and with the first end of the axle fixedly attached to the superior surface of the base plate, the base assembly also comprising an elongate second component, said second component comprising an elongate element with a first end and a second end, and with a superior surface and an inferior surface, and with the inferior surface of the second end of the elongate element comprising an orifice for cooperating rotatably with the axle of the base plate, and with the superior surface of the second component comprising a longitudinal arc-like configuration, and with the inferior surface of the second component being contiguous in a rotatable sliding relationship with the superior surface of the base plate, the base assembly also comprising a third elongate component comprising a first end and a second end, and with a superior surface and an inferior surface, and with the inferior surface of the third elongate component comprising arc-like surfaces having a longitudinal arc-like configuration that is congruent with, and in apposition with, the superior surface of the second component and with a horizontal line through the center of rotation of the arc-like surfaces comprising a horizontal axis and with said horizontal axis intersecting with the vertical axis of the axle of the base plate, the base assembly also comprising an elongate fourth component comprising a drilling device support, said support comprising a superior surface and an inferior surface, and with means for the releasable attachment of the inferior surface of the fourth component to the superior surface of the third component, said means comprising a threaded fastener, and with the superior surface of the elongate fourth component comprising a targeting assembly, said targeting assembly comprising an elongate member with a first end and a second end, and a superior surface and an inferior surface, the targeting assembly comprising an elongate rod with a first end and a second end, the elongate rod being attached to the second end of the elongate fourth component, and with a beadlike target attached to the second end of the rod, said target positioned at the intersecting axes of horizontal and vertical axes of rotation of the bi-rotatable base, and on a longitudinal midline of the superior surface of the elongate fourth component, wherein the bead-like target is positionable in apposition to a surface marking on a surface of a leg, said marking indicative of the axis of the x-ray beam passing through said marking and said distal openings of the intramedullary nail that has been inserted into the cavity of the tubular long bone, the apparatus also comprising a laser source located at the first end of the elongate fourth component, positioned with its beam parallel to the longitudinal axis of the superior surface of the elongate fourth component, and coaxial with the longitudinal line through the bead-like target, and with said beam directed away from the target positioned at the second end of the elongate fourth component, and with said elongate fourth component removable after the adjustment of the base assembly, the apparatus also comprising a sled mounted motorized drill and a sled, said sled comprising an elongate member with a superior surface and an inferior surface, and with the inferior surface of the elongate member of the sled of the configured with a sliding cooperation with the superior surface of the third component along their longitudinal axes, and with the superior surface comprising a circular clamp, said clamp configured to maintain said motorized drill in a longitudinal position, with the central longitudinal axis of the drill coaxial with said line through said bead-like target, wherein the baseplate comprises means for the releasable attachment to a floor mounted adjustable support stand with an adjustable head.

6. An orthopedic apparatus of claim 5 wherein the apparatus is comprised of metal, plastic, or reinforced polymer and capable of being sterilized.

* * * * *